United States Patent [19]

Gelinas et al.

[11] Patent Number: 4,522,212

[45] Date of Patent: Jun. 11, 1985

[54] ENDOCARDIAL ELECTRODE

[75] Inventors: Sandra L. Gelinas, North Attleboro; Daniel G. Cerundolo, Hingham; John E. Abele, Concord, all of Mass.

[73] Assignee: Mansfield Scientific, Inc., Mansfield, Mass.

[21] Appl. No.: 551,243

[22] Filed: Nov. 14, 1983

[51] Int. Cl.³ .............................................. A61D 5/04
[52] U.S. Cl. ................................ 128/642; 128/419 P; 128/784; 128/786
[58] Field of Search ............................... 128/695–696, 128/784–786, 802, 419 P, 642

[56] References Cited

U.S. PATENT DOCUMENTS

| | | | |
|---|---|---|---|
| 3,347,224 | 10/1967 | Adams | 128/691 |
| 3,814,104 | 6/1974 | Irnich et al. | 128/419 P |
| 3,825,015 | 7/1974 | Berkovits | 128/786 |
| 3,865,118 | 2/1975 | Bures | 128/786 |
| 3,866,615 | 2/1975 | Hewson | 128/784 |
| 3,949,757 | 4/1976 | Sabel | 128/419 P |
| 4,057,067 | 11/1977 | Lajos | 128/419 P |
| 4,112,952 | 9/1978 | Thomas et al. | 128/419 P |
| 4,164,939 | 8/1979 | Kolin | 128/696 |
| 4,289,138 | 9/1981 | Halvorsen | 128/642 |

FOREIGN PATENT DOCUMENTS

| | | | |
|---|---|---|---|
| 2605590 | 8/1977 | Fed. Rep. of Germany | 128/419 P |
| 2504394 | 10/1982 | France | 128/419 P |
| 246004 | 11/1969 | U.S.S.R. | 128/419 P |

OTHER PUBLICATIONS

Horowitz et al., "Ventricular Resection Guided by Epicardial and Endocardial Mapping for the Treatment of Recurrent Ventricular Tachycardia", N.E.J.M., vol. 302, No. 11, Mar. 13, 1980, pp. 589–593.

Primary Examiner—William E. Kamm
Assistant Examiner—Mitchell J. Shein

[57] ABSTRACT

An endocardial electrode assembly of three or more spring legs to be inserted into the heart, sets of electrodes on respective spring legs comprising distinctive geometrical patterns, over the ventricle-contacting span of the legs, such that the active sets of electrodes provide recognizable patterns when within a ventricle of the heart and viewed with a fluoroscope, the respective locations of at least some of the electrodes of these patterns being staggered relative to electrodes on other legs in the manner to reduce lateral clumping, thus to permit the numerous electrodes to be housed in a catheter sized to be conveniently introduced into the heart.

16 Claims, 18 Drawing Figures

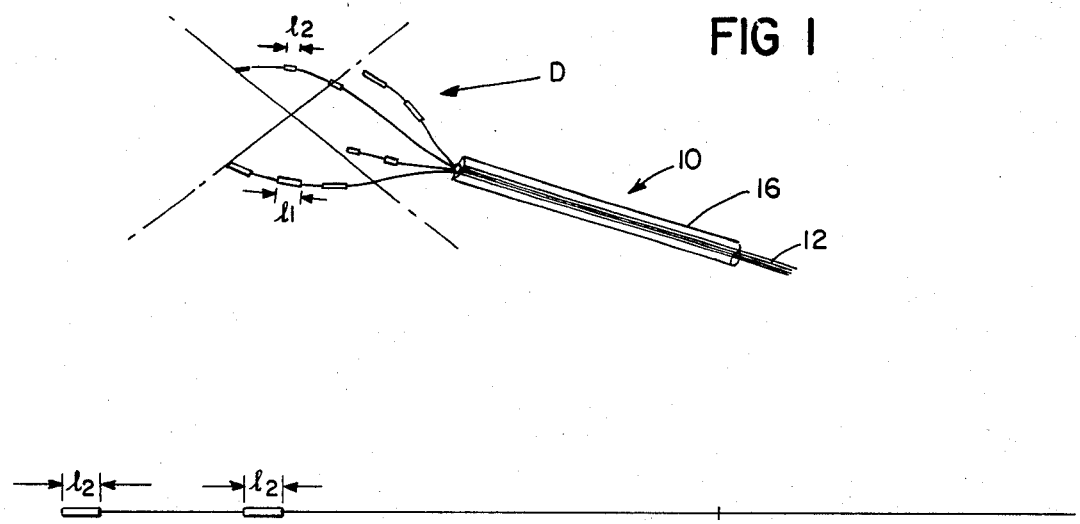
FIG 1
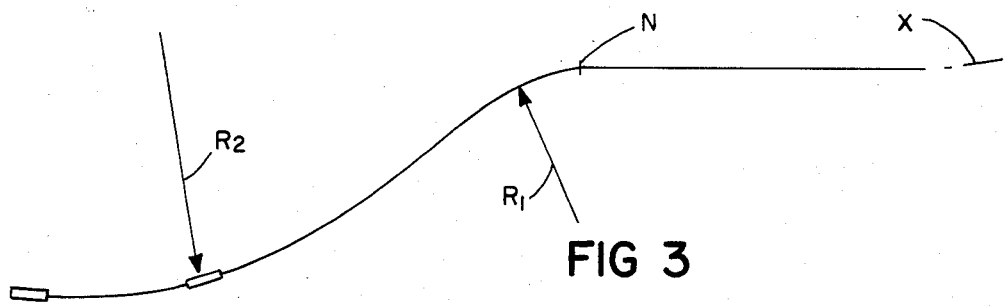
FIG 2
FIG 3
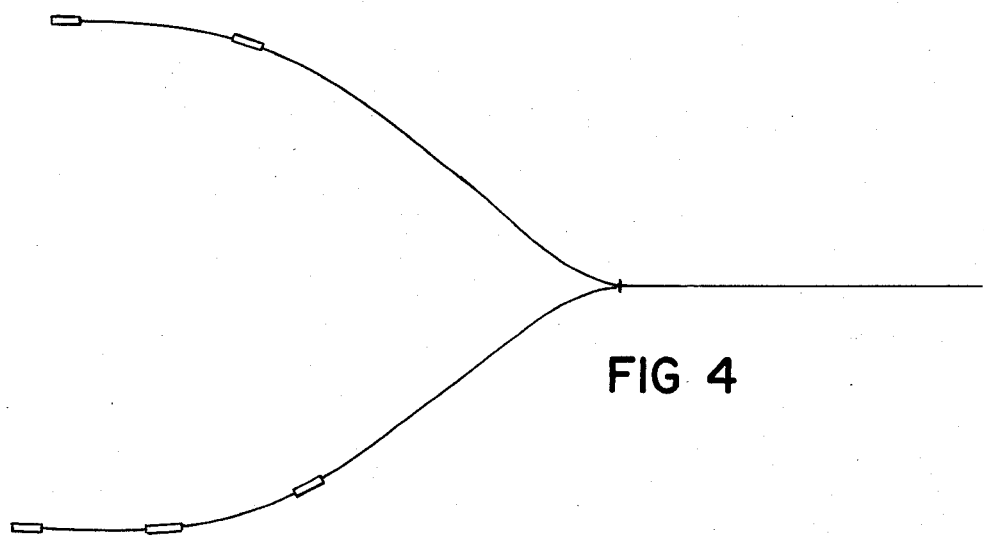
FIG 4

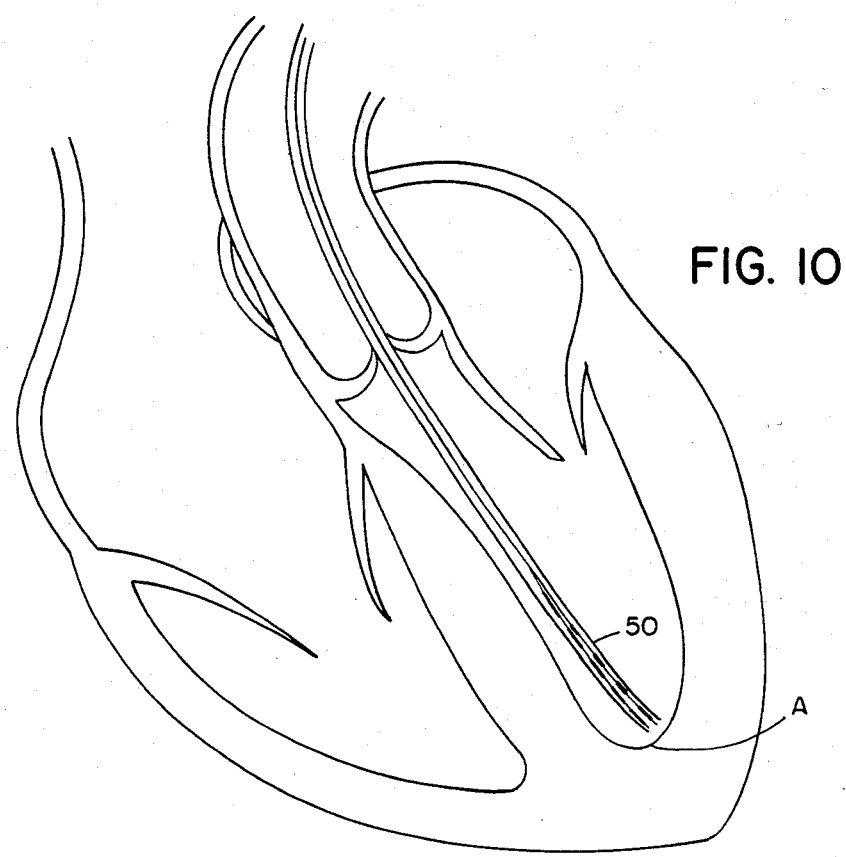
FIG. 10
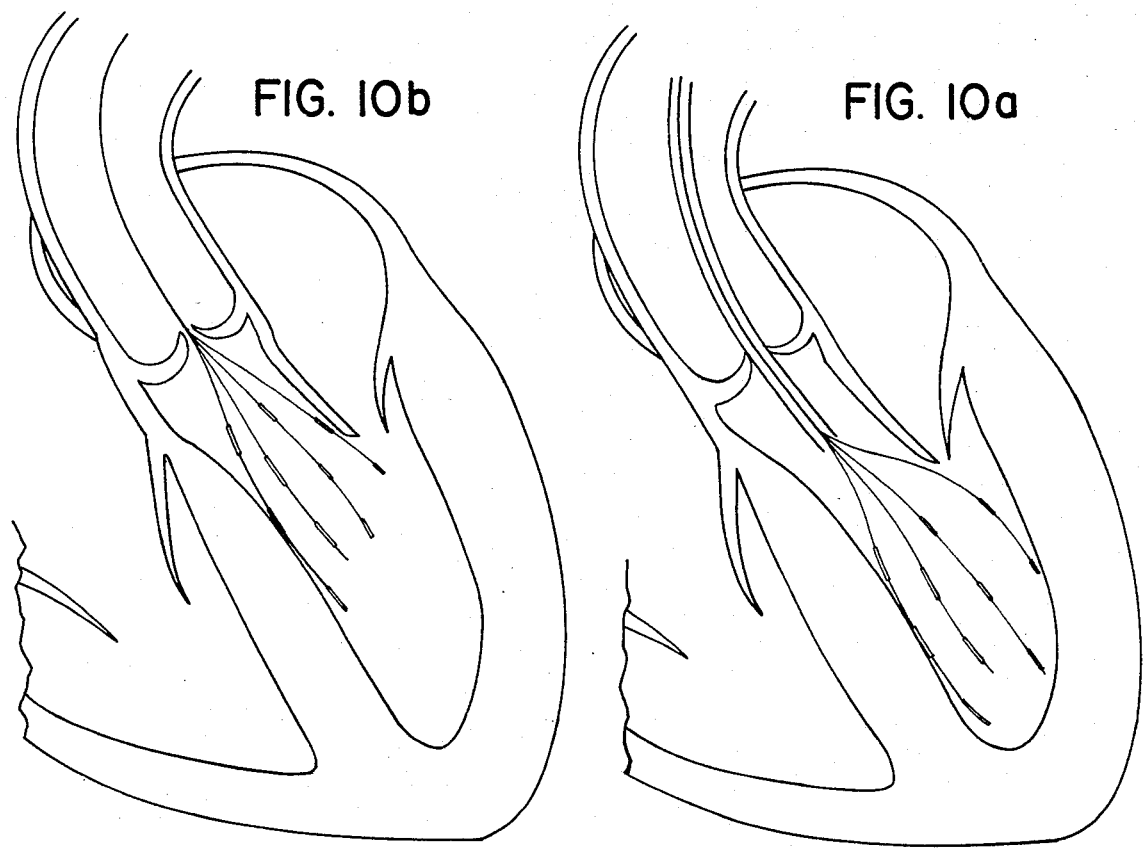
FIG. 10b
FIG. 10a

ENDOCARDIAL ELECTRODE

BACKGROUND OF THE INVENTION

This invention relates to endocardial electrodes for electrical contact with an array of points on the inner wall of the heart of a living being. Such contact has long been recognized to be desirable for a number of purposes. One example is mapping of the muscle activation sequence of endocardial tissue. In this case, an array of electrodes is placed via a catheter within the left or right ventricle and, as the heart beats, a multichannel recorder simultaneously records respective electrograms of the sequence of potentials appearing at the individual electrodes. While this is occurring, the cardiologist seeks, by use of a fluoroscope, to determine the location of the various contact points of the electrodes with the ventricular wall, thus to correlate these locations with respective electrograms. If he is successful, he may find a point of initiation of heart arrythmia, which may then be treated. Early attempts of doing this were of limited value because of the few, and poor distribution of, points at which simultaneous readings could be taken.

Proposals have been made for achieving more contact points around the ventricle, such as by use of a compressible three-dimensional basket-like array of proximally and distally connected spring arms carrying electrodes, or by use of a series of free-ended, s-curved spring arms that spread distally, tulip-like, from a proximal connection point. Any attempt to implement such approaches encounters serious problems. One is the difficulty (even if some radio-opaque marking is employed) of fluoroscopically indentifying individual electrodes of such a more numerous, three-dimensional array within the heart to correlate the location of the many electrodes with respective electrograms; another is the difficulty of introducing such an elaborated assembly into the heart in a conventionally sized cardiac catheter, in a way that the assembly can spring into the desired distributed wall contact when released; another is the multiple opportunity for confusion of the cardiologist as he seeks to rapidly conduct this complex examination of the patient.

Because of such problems, the use of the three-dimensional, multi-electrode technique, though of considerable theoretical benefit, has not been acceptably implemented.

The present invention is direction to overcoming such problems, and to achieve practical use of a three-dimensional array of a large number of electrodes within a ventricle of the heart, comprised e.g. upwards of six or preferably considerably more electrodes.

SUMMARY OF THE INVENTION

The invention is directed to an endocardial electrode assembly comprising three or more elongated insulated spring wire legs joined together at least in a region spaced from the distal end of the assembly, the assembly constructed to be inserted into the heart while surrounded by a distal portion of a catheter, and to be exposed to active position by proximal movement of the catheter to a withdrawn position relative to the spring leg assembly, the spring legs comprising insulated conductors connected to respective sets of spaced electrodes carried by the legs, these spring legs having predetermined shape to spring relatively apart to cause the electrodes to engage with wall tissue within a cavity of the heart, in the manner that a three-dimensional array of spaced electrode contact points can be simultaneously made with the heart wall.

According to the present invention, the sets of electrodes on respective spring legs comprise distinctive geometrical patterns over the ventricle-contacting span of the legs, preferably within a span of a few centimeters from the distal end of the assembly, such that the active sets of electrodes provide recognizable patterns when within a ventricle of the heart and viewed with a fluoroscope, the respective locations of at least some of the electrodes of these patterns also being staggered relative to electrodes on other legs in the manner to reduce lateral clumping, thus to permit the numerous electrodes to be housed in a catheter of size that can practically be introduced into the heart. While this broad aspect of the invention is applicable to various assemblies of spring legs, it is of particular importance in making it possible to achieve success with a many-legged, tulip-shaped assembly of free ended spring legs. In this respect, the invention preferably employs four or more free-ended spring legs assembled in the manner to provide a three dimensional array of simultaneous spaced electrode contact points with the heart wall, the portion of each spring leg immediately distal of the catheter when the catheter is in the withdrawn position being curved concavely outwardly from a projected center axis of the assembly with radius of curvature less than the critical radius, portions of the spring legs further distal therefrom being curved convexly with a greater radius, the critical radius of curvature being of the order of one centimeter, selected relative to the thickness and substance of the spring leg, the size of the assembly and the internal diameter of the catheter to enable straightening of the spring legs to conform to the interior dimension of the catheter within the elastic limit of the spring legs, whereby pulling of the spring leg assembly into the catheter and subsequent withdrawal of the catheter to expose the spring legs results in expansion of the spring legs, in the unconfined state, substantially to the original predetermined geometry of the spring legs. Further, by staggering a majority of the electrodes in the distal region of the assembly relative to electrodes on another leg to reduce lateral clumping, it has been possible to map the endocardium of a ventricle with an assembly of ten electrodes.

Preferably, to achieve this tulip construction, individual spring arms are separately formed, pairs are then joined in opposition in a plane, and two sets of pairs are then joined at right angles to one another.

It is highly preferred that distinctive feature of the patterns extend through the array so that even if a leg is partially mashed, there is still some likelihood of being able to distinguish it from another leg lying close to it in the fluoroscopic view.

In preferred embodiments of the above various aspects of the invention, the electrodes are of at least two visually recognizable different sizes, these sizes being distributed in a manner contributing to distinctive geometrical patterns; there are at least two different numbers of electrodes on the set of legs to contribute to the distinctive geometrical patterns; and preferably both the sizes and the number of electrodes vary over the set of legs to contribute to the distinctive geometrical patterns. In some cases electrode spacing can also be used to contribute to the distinctiveness of the patterns.

Preferably, in certain instances, a geometrical pattern is linear along a respective leg while in other instances, at least some of the electrodes are disposed on individual sub-legs which flare from respective main legs. In the latter case, advantageously the number of the sub-legs may vary across the set of legs to contribute to the differing geometrical patterns.

According to another aspect of the invention, the proximal terminations of the conductors are provided with connectors arranged in predetermined patterns suggestive of the patterns on the spring arms with which they are related, helping to enable the cardiologist, at a glance, to determine the relationship of the end connectors with what he is seeing via the fluoroscope.

IN THE DRAWINGS

FIG. 1 is a diagramatic, perspective view of a first preferred embodiment of the invention, while FIGS. 2, 3 and 4 diagramatically illustrate steps in the formation of the leg assembly of the embodiment of FIG. 1, FIG. 5 diagramatically illustrates the relationship of the various electrode sets to one another, while FIGS. 6 and 7 illustrate steps in the connection of the electrodes into the wire assembly;

FIG. 8 is a diagrammatic view of a patient undergoing fluoroscopy with the embodiment of FIG. 1 in place in the left ventricle of the heart while

FIG. 10 illustrates the position of the catheter and electrode assembly, with the distal end at the apex of the ventricle, after insertion and prior to withdrawal of the catheter;

FIG. 10a is a view similar to FIG. 10 of the catheter withdrawn and the tulip-shaped assembly expanded within the left ventricle;

FIG. 10b is a view similar to FIGS. 10 and 10a with the assembly partially withdrawn for the purpose of mapping upper portions of the left ventricle;

Figure 5:
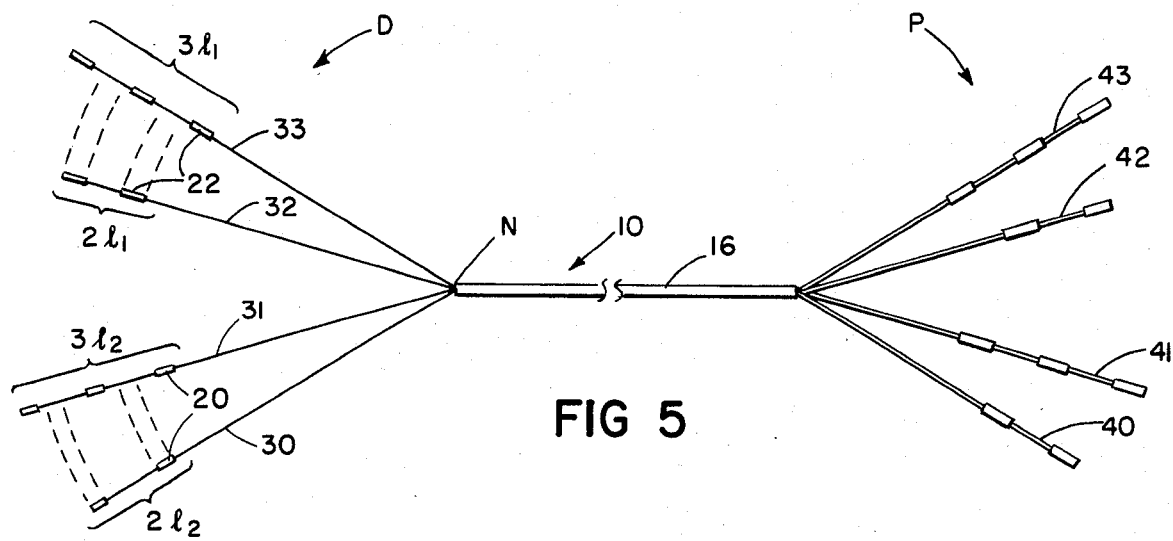

FIGS. 11, 12, 13, and 14 are views similar to FIG. 5 of further embodiments of the invention.

DESCRIPTION OF PREFERRED EMBODIMENTS

Referring to FIGS. 1 and 5, the main body 10 of the assembly consists of ten individual wires 12, each individually insulated at 14 (see FIG. 6) and held together in this embodiment with heat shrink tubing 16. The distal and proximal ends D and P respectively of the main body 10 terminate in four limbs or legs 30, 31, 32, 33 and 40, 41, 42 and 43, respectively. Two legs of each set (30, 32; 40, 42) each has two wires and two legs of each set (31, 33; 41, 43) each has three wires. Each group is held together in this embodiment with smaller shrink tubing 18. All wires at the distal end terminate with an electrode ferrule 19 (stainless steel band) connected onto a bare end of a wire 14. A two wire and a three wire leg (30, 31) has one size of electrode (short electrodes 20) and a two wire and a three wire leg (32, 33) has electrodes about twice the size of the first set, (long electrodes 22). In this embodiment, the short electrodes are 3 mm. in length and the long electrode. 5 mm. The electrode ferrules on each leg are spaced in this embodiment equally, 1 cm. from each other and are staggered in relation to the ferrules of a neighboring leg (see projection lines, FIG. 5), to reduce lateral clumping, such that they will fit a small inner diameter of a conventional cardiac catheter 50 (FIG. 10) of about 0.060 inch diameter when collapsed.

The proximal legs hook up to electrical connector box 52 (FIG. 8) which plugs into a stimulation and recording system 54 for mapping of electrical activity when the electrodes lie in the ventricle.

Figure 8:
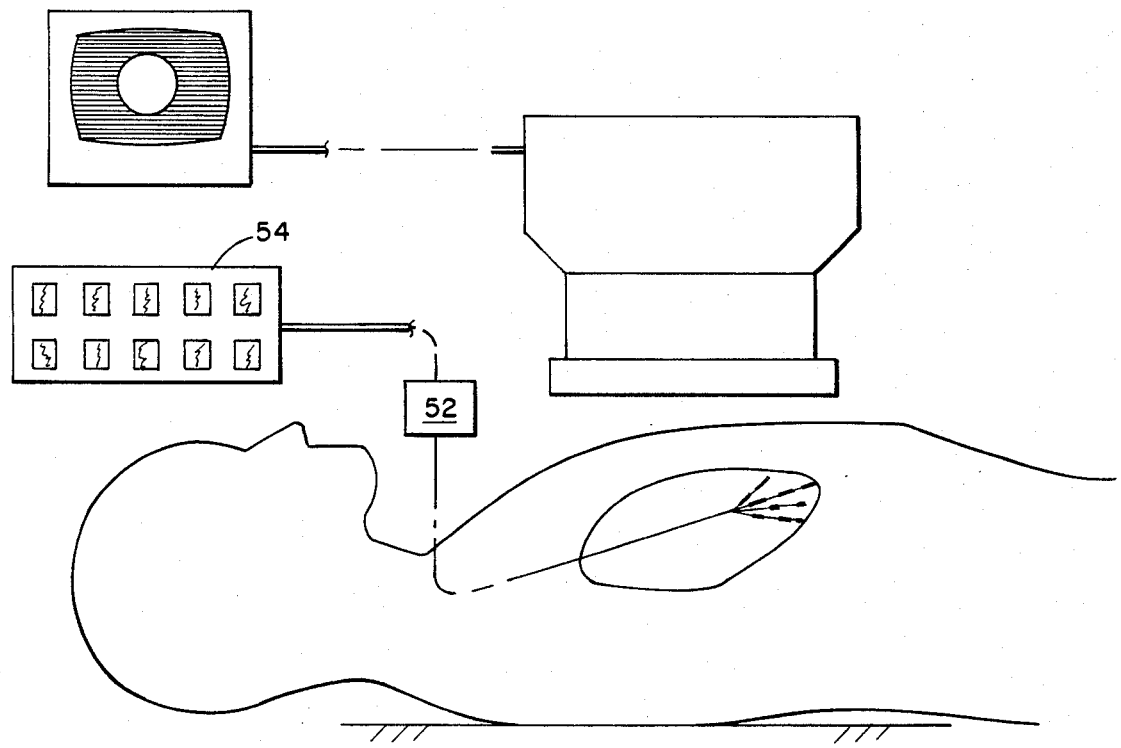
Figure 11:
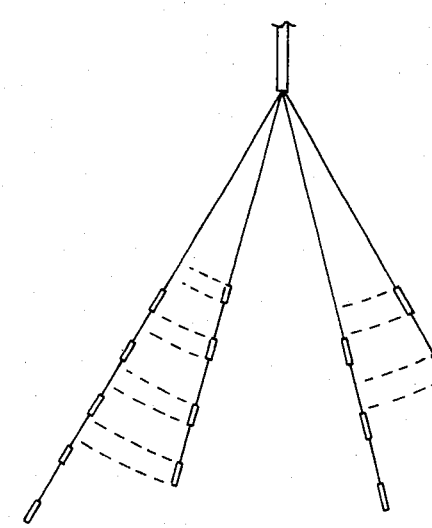
Figure 12:
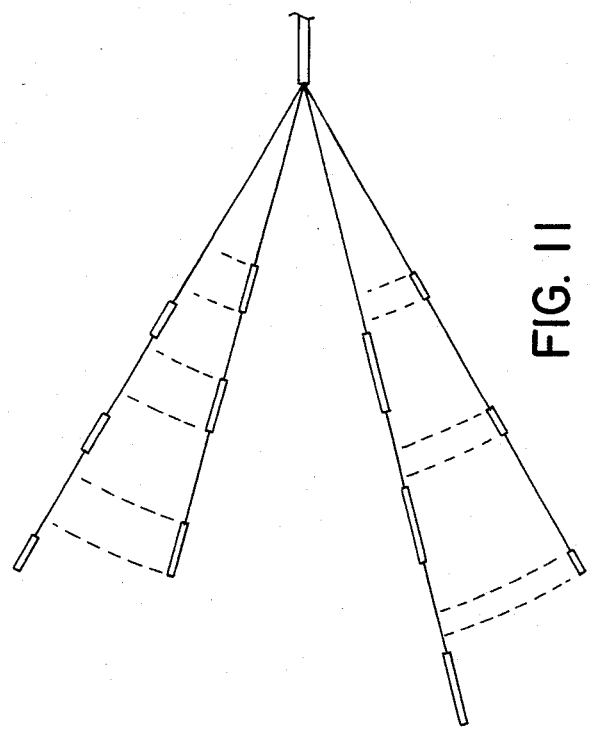

Referring to FIGS. 8 and 10, the electrode assembly is introduced subcutaneously with the help of a conventional cardiac placement catheter. It is correctly positioned by advancing the catheter 50 (which contains the electrode assembly) to the apex A, FIG. 10, of the ventricle, at which point the catheter 50 is retracted to the position of FIG. 10a, allowing the release of the spring legs. This may be used for either left or right ventricular studies. By use of a catheter 50 with torsional stiffness, the array of electrodes may be rotated within the ventricle to a series of successive positions, and may be partially withdrawn, see FIG. 10b, for further contact with upper portions of the ventricular wall, all with the aid of the distinctive patterns that extend to the distal ends of the legs.

Figure 13:
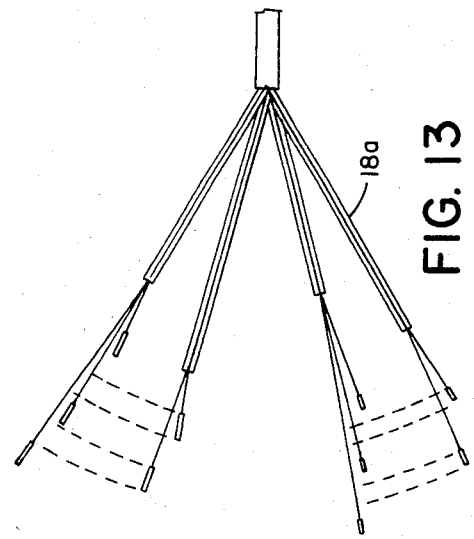
Figure 14:
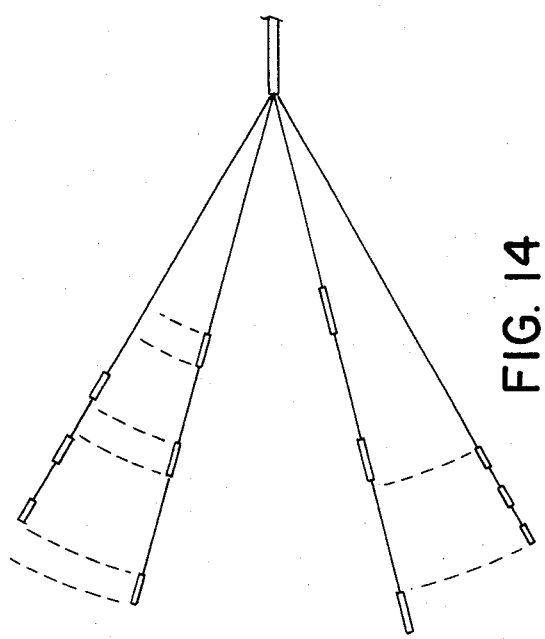

In the alternative embodiment of FIG. 13 the connecting shrink tubing 18a at the distal end does not extend to the entire length of the electrodes, rather it stops to allow each electrode a small flare from the others ("flare-on-flare").

The connector (proximal) end is constructed so that all wires in the group terminate at the same end point and are electrically connected to stainless steel ferrules of deliberate by different numbers in correlation with the different numbers of electrodes on the distal ends of the legs, as an important identification aid to the caridologist.

The significant features of this mapping electrode system include the fluoroscopically identifiable legs having three and two electrodes of one size and three and two electrodes of another size, the termination points of each electrode enabling individual flare on flare where desired, the spacing of the electrodes being such that they fit together when collapsed to reduce overall diameter (a feature known per se for individual electrodes, from Halvorsen U.S. Pat. No. 4,289,138). The present invention significantly extends the practical capabilities of electrodes to map the area within the ventricle.

Figure 9:
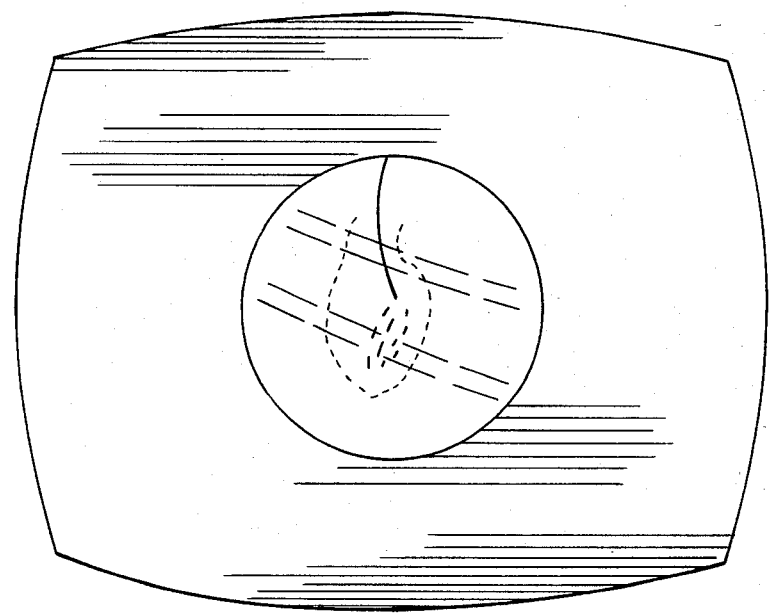
FIG. 9 is a magnified view of the TV monitor of FIG. 8.

Because the presently preferred embodiment includes two different sizes of electrodes and two different numbers of each size, each limb presents a distinguishable linear pattern from the other upon fluoroscopy, see FIG. 9. The numerous, identifiable electrodes allow more recordable electrograms with accuracy of localizaton. The multiple arms allow for simultaneous recording and/or stimulation of multiple three-dimensional spaced points on the walls of the endocardium.

DETAILS OF MANUFACTURE

Figure 6:
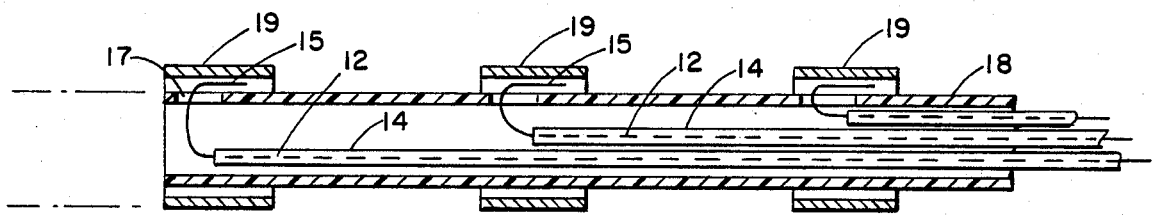

In a typical assembly procedure according to the invention, the individual conductors 12 are stainless steel spring wire of 0.007 to 0.009 inch diameter, coated with urethane insulation 14 of e.g., 0.001 inch thickness. The selected number of wires is cut to appropriately different lengths and the insulation 14 is stripped from the ends to provide bare connection wire ends 15. A shrink tubing 18, e.g. high shrink polyethylene of 0.002 inches wall thickness, is slipped over each set of conductors to the nodal point N. This tubing is then skived at appropriate points and the ends 15 of the wires are then led out of the registering openings 17 and bent back, as shown in FIG. 6. The tubing is then heat shrunk, and electrode ferrules 19 are applied over the bare wire ends, and swagged down to correspond with the outer diameter of the shrink tubing 18, see FIG. 7. The proximal end connectors are similarly applied.

Each leg is bent to the desired shape as shown in FIG. 3, with the leg bending concavely outwardly from the nodal point N with radium $R_1$ of about 1 centimeter, and then bent convexly back with larger Radius $R_2$, thus to form an S curve, terminating on a line approximately parallel with but off-set from Axis X. Care is taken, with reference to the chosen material of the legs and the size of the introducer catheter, not to exceed the elastic limit of the wires during bending and during insertion into the catheter.

Referring to FIG. 4, two of such legs are joined together back to back in a pane at an adhesive joint in the nodal region N, then with the aid of an appropriate jig, two such sets are joined at 90° to each other, again with adhesive being applied in the nodal region, to set the angles of the legs with respect to one another. The proximal portions of these conductors are then aligned with one another and are let through a further length of shrink tubing 16 up to nodal point N, tubing 16 being sized to allow protrusion of the proximal end portions of the various conductors. Thereupon, the introducing catheter 50 sheath can be slipped over the assembly, and, if not done previously, the proximal connecter ferrules can be attached in mating numbers on the legs, to match the numbers on the proximal ends of the respective legs. These proximal connectors may be marked "long" and "short" to correspond with respective distal electrodes, or the proximal connectors themselves can be correspondingly long or short in dimension for ease of identification.

Figure 7:
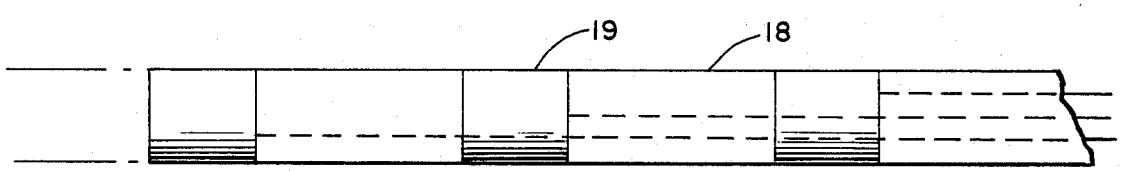
FIGS. 7a and 7b illustrate alternative means of manufacture of the electrode assembly.
Figure 7A:
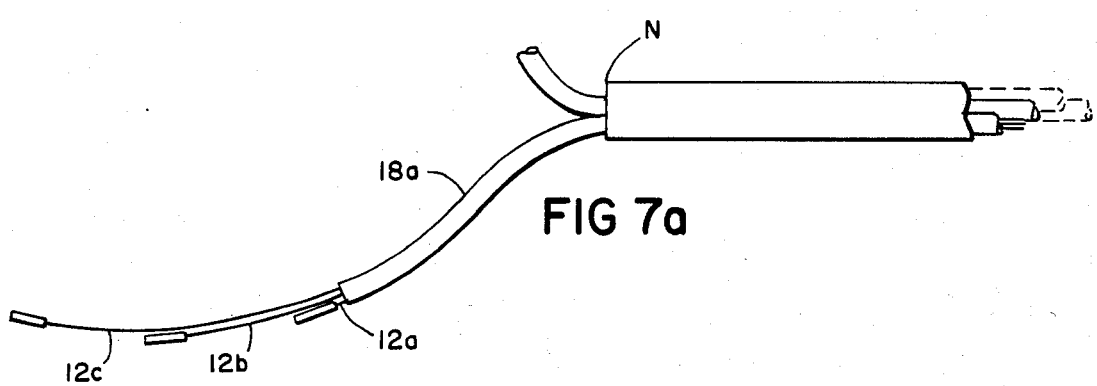

Referring to FIG. 7a, to achieve a "flare-on-flare" the tubing 18a may terminate at the first elecrode, leaving the protruding portions 12a, 12b and 12c of the insulated wires to freely protrude at varying distances. If desired, bends can be introduced to these flaring portions to achieve further distribution of the electrode contact points.

Figure 7B:
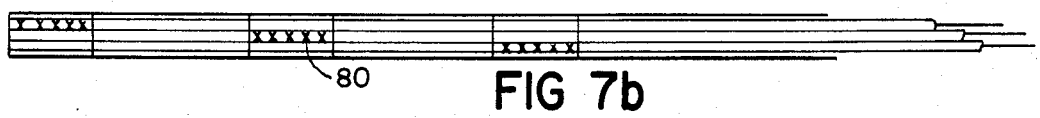

Referring to FIG. 7b, as an alternative to the assembly procedure of FIGS. 6 and 7, each wire 12 extends for the full length of the respective wire. The wires are stripped at different points, the overlying shrink tube is correspondingly skived and conductive adhesive 8 is introduced to effect electrical contact between the respective wires and their connectors. The advantage of such construction is that the full length of the leg may be strengthened by the full extension of each wire, despite the fact that the electrodes for some of the wires are placed further up the assembly.

OTHER EMBODIMENTS

Variations in the details of the implementation of the invention are possible in numerous ways, e.g., in respect of the selection of tubing, wire, wire insulation, connecting ferrules, electrodes, adhesive and possible use of a transition piece between the body and electrode limbs to maintain desired angular relationship of the legs. Alternate methods of connecting the electrodes, ferrules, and grouping of wires can be acceptably employed. Design changes that may occur include number of limbs, number of electrodes, size of electrodes and the shape of the usable end. The limbs may be preformed to a variety of shapes such as a basket, tulip or even reverse flare.

For example, FIGS. 11–14 illustrate variations within the general concept of the invention, in this case employing four free-ended limbs, with mating electrode placement (see projection lines) between pairs of limbs to reduce lateral clumping.

We claim:

1. An endocardial electrode assembly, said assembly comprising three or more elongated insulated wire spring legs joined together at least in a region spaced from the distal end of said assembly, said assembly constructed to be inserted into the heart while surrounded by a distal portion of a catheter, and to be exposed to active position by proximal movement of the catheter to a partially withdrawn position relative to said assembly.

the legs comprising insulated conductors connected to respective sets of spaced electrodes carried by the legs, said spring legs having predetermined shape and position to spring relatively apart to cause the electrodes to engage with wall tissue within a cavity of the heart, in the manner that a three dimensional array of spaced electrode contact points can be simultaneously made with the wall of the beating heart.

the sets of electrodes on respective spring legs comprising distinctive geometrical patterns, over the ventricle-contacting span of the legs, such that the active sets of electrodes provide recognizable patterns when within a ventricle of the heart and viewed with a fluoroscope, the respective locations of at least some of the electrodes of these patterns being staggered relative to electrodes on other legs in the manner to reduce lateral clumping, thus to permit the numerous electrodes to be housed in a catheter sized to be conveniently introduced into the heart.

2. For use in determining the muscle activation sequence of tissue of the heart and the like, an endocardial electrode assembly comprising a multiplicity of elongated insulated wire probes joined together in a region spaced from distal ends of said probes, said probes constructed to be inserted into the heart while surrounded by a distal portion of said catheter, and to be exposed to active position by proximal movement of the catheter to a partially withdrawn position relative to said assembly, said assembly comprising three or more free-ended spring legs, the spring legs comprising insulated conductors connected to respective sets of spaced electrodes carried by the legs, said spring legs having predetermined shape and position to spring relatively apart to cause the electrodes to engage with wall tissue within a cavity of the heart, in the manner that a three dimensional array of spaced electrode contact points can be simultaneously made with the heart wall, the portion of each spring leg immediately distal of said catheter when the catheter is in the withdrawn position being curved concavely outwardly from a projected center axis of said assembly with radius of curvature less than the critical radius, portions of said spring legs further distal therefrom being curved convexly with a greater radius, said critical radius of curvature being of the order of one centimeter, selected relative to the thickness and substance of said spring leg, the size of said assembly and the internal diameter of said catheter to enable straightening of said spring legs to conform to the interior dimension of said catheter within the elastic limit of said spring legs, whereby pulling of said spring leg assembly into said catheter during manufacture and subsequent withdrawal of said catheter to expose said spring legs results in expansion of said spring legs, in the unconfined state, substantially to the original predetermined geometry of said spring legs, the sets of electrodes on respective spring legs comprising distinctive geometrical patterns over the ventricle-contacting span of the legs such that the active sets of electrodes provide recognizable patterns when within a ventricle of the heart and viewed with a fluoroscope, the respective locations of a majority of the electrodes in the distal region of the assembly being staggered with respect to electrodes on at least one other leg in the manner to reduce lateral clumping so that the electrodes can be housed in a catheter that can conveniently be introduced into the heart.

3. The endocardial electrode assembly of claim 1 or 2 wherein each of said patterns has at least one distinguishing attribute extending substantially throughout the range of its respective set of electrodes.

4. The endocardial electrode assembly of claim 1 or 2 wherein at least most of the electrodes of the assembly each contributes a part to the distinctiveness of the pattern of the respective leg in a manner that aids in enabling its leg to be fluoroscopically distinguished from a corresponding region of at least one other leg.

5. The endocardial electrode assembly of claim 1 or 2 wherein four pre-shaped spring legs extend from a common nodal point with 90° spacing therebetween.

6. The endocardial electrode assembly of claim 5 wherein ten or more electrodes are carried by said assembly.

7. The endocardial electrode assembly of claim 1 or 2 wherein said electrodes are of at least two visually different sizes, said sizes distributed in a manner contributing to said distinctive geometrical patterns.

8. The endocardial electrode assembly of claim 7 wherein the size of electrodes of a given leg differs from the size of the electrodes on the legs adjacent to said leg in the array.

9. The endocardial electrode assembly of claim 1 or 2 wherein there are at least two different numbers of electrodes on said set of legs to contribute to said distinctive geometrical patterns.

10. The endocardial electrode assembly of claim 9 wherein the number of electrodes of a given leg differs from the number of electrodes in the leg generally opposite from it in the array.

11. The endocardial electrode assembly of claim 1 or 2 wherein both the sizes and the number of electrodes vary over the set of said legs to contribute to said distinctive geometrical patterns.

12. The endocardial electrode assembly of claim 1 or 2 herein said geometrical patterns are linear along respective legs.

13. The endocardial electrode assembly of claim 1 or 2 wherein, along at least one of the legs, at least some of said electrodes are disposed on individual sub-legs which flare from the respective leg.

14. The assembly of claim 13 wherein the number of said sub-legs varies across said set of legs to contribute to the differing geometrical patterns.

15. The endocardial electrode assembly of claim 1 or 2 wherein the proximal terminations of the conductors for the respective legs are separate, and provided with connectors arranged in predetermined patterns suggestive of the patterns on the spring legs with which they are related, said connectors serving to help the cardiologist, at a glance, to determine the relationship of the end connectors with what he is seeing via the fluoroscope.

16. The endocardial electrode assembly of claim 1 or 2 wherein a said spring leg is comprised of multiple conductors, each of said conductors being insulated and extending the full length of said leg, the electrodes being spaced along said leg, with connection means extending through the insulation of each respective conductor to the respective electrode.

* * * * *